United States Patent [19]
Geary

[11] Patent Number: 5,254,084
[45] Date of Patent: Oct. 19, 1993

[54] PERITONEAL CATHETER DEVICE FOR DIALYSIS

[76] Inventor: Gregory L. Geary, 12355 N.W. Maple Hill La., Portland, Oreg. 97229

[21] Appl. No.: 37,347

[22] Filed: Mar. 26, 1993

[51] Int. Cl.$^5$ .............................................. A61M 1/00
[52] U.S. Cl. ................................ 604/29; 604/280
[58] Field of Search ............... 604/29, 27, 48, 90, 604/93, 96, 175, 286, 43, 280

[56] References Cited

U.S. PATENT DOCUMENTS

| | | | |
|---|---|---|---|
| 3,384,089 | 5/1968 | Shriner | 604/280 |
| 4,184,497 | 1/1980 | Kolff et al. | 131/213 A |
| 4,368,737 | 1/1983 | Ash | 604/125 |
| 4,417,888 | 11/1983 | Cosentino et al. | 604/125 |
| 4,437,856 | 3/1984 | Valli | 604/29 |
| 4,681,564 | 7/1987 | Landreneau | 604/280 |
| 4,717,379 | 1/1988 | Ekholmer | 604/43 |
| 5,057,075 | 10/1991 | Moncrief et al. | 604/49 |
| 5,090,954 | 2/1992 | Geary | 604/29 |
| 5,098,413 | 3/1992 | Trudell et al. | 604/29 |
| 5,100,395 | 3/1992 | Rosenberg | 604/284 |
| 5,116,310 | 5/1992 | Seder et al. | 604/43 |

FOREIGN PATENT DOCUMENTS

| | | | |
|---|---|---|---|
| 1457934 | 2/1989 | U.S.S.R. | 604/280 |
| 9200113 | 1/1992 | World Int. Prop. O. | 604/280 |

*Primary Examiner*—John G. Weiss
*Attorney, Agent, or Firm*—Kolisch, Hartwell, Dickinson, McCormack & Heuser

[57] ABSTRACT

A flexible peritoneal catheter device for dialysis comprising a ductwork of multiple tubes enclosed within a fluid permeable envelope structure, the tubes having holes therein for fluid flow and the envelope structure having slit shaped holes therein to allow fluid flow but discouraging tissue adherence.

15 Claims, 1 Drawing Sheet

PERITONEAL CATHETER DEVICE FOR DIALYSIS

BACKGROUND AND SUMMARY OF THE INVENTION

This invention relates to a peritoneal catheter device for dialysis or the like treatments in the abdominal cavity.

Peritoneal dialysis is performed by implanting into the peritoneal, or abdominal cavity, a peritoneal dialysis catheter. The catheter may be connected via a tube to a dialysis port. The dialysis port can be positioned interior or exterior to the patient's body, as shown in U.S. Pat. No. 5,090,954, issued to Geary, the inventor herein. Dialysis fluid may be injected into the dialysis port or the external portion of the catheter, which then travels to the catheter through a connecting conduit, and thereby out the catheter into the peritoneal cavity. Once in the peritoneal cavity the dialysis fluid bathes the peritoneal surfaces within the cavity, whereby the chemical and physical interactions of dialysis take place. After the exchange of fluids, suction is applied to the connecting conduit which pulls the dialysis fluid, containing the exchanged impurities, out of the peritoneal through the catheter, ending the dialysis procedure.

In response to the object of increasing a catheter's outer surface area, prior art devices with large surface areas were developed. In particular, U.S. Pat. No. 4,437,856, issued to Valli, discloses a peritoneal catheter device for dialysis with an expandable outer surface. FIG. 2 of Valli discloses a catheter 1 having an inflatable membrane 11 which surrounds a single inner catheter 2. Inflation of the balloon shaped outer membrane 11 increases the effective fluid contact surface area of the inner catheter 2, thereby increasing the effectiveness of the dialysis procedure. As shown in Valli at FIG. 2, outer membrane 11 has round holes 11' to allow passage of the dialysing liquid from the inner catheter 2 to the outer surface of membrane 11.

One of the major problems associated with current peritoneal dialysis is poor flow through the catheter into the peritoneal. Most of the time, this is due to particulate matter trapped within and around the catheter which blocks holes in the catheter through which the fluid flows. The particulate matter is often formed of protein in the form of fibrin, which readily adheres to current catheters and the holes therein. Another source of catheter blockage is the greater omentum, a large apron of fatty tissue that serves to insulate inflammation or other foreign objects within the peritoneal cavity. The omentum often becomes adhered to the catheter, occluding the fluid channels. Yet another problem is the bowel and the intestines, which become entangled with the free floating intraperitoneal catheters currently used. Still other sources of particulate matter are the organs themselves, protein globules and tissue pieces broken off the omentum.

Balloon shaped catheters, as disclosed in Valli, often become entangled with the omentum, bowel, intestines or other organs. In addition, catheters with round holes for the passage of dialysis fluid, as shown in Valli, become clogged because particulate matter and protein in the form of fibrin readily adheres to such round holes.

The catheter of this invention overcomes these problems with the prior art by having a large surface area for fluid exchange, and a generally flat, elongate outer shape, so that the catheter may be placed against the peritoneal wall, avoiding the problem of entanglement with the omentum, bowel, intestines and other organs. In addition, the present invention overcomes the problem of fluid passageway occlusion by disclosing a design which inhibits occlusion by particulate matter. This is accomplished by incorporating a system of multitubing channels sandwiched between a non-adherent outer surface that discourages tissue or fibrin adherence. In addition, the outer surface has coaptable slits, instead of round holes, to further discourage tissue or fibrin adherence.

A design limitation of peritoneal catheters is that they must be compact in shape to fit comfortably in the patient's peritoneal cavity. In addition, flexible catheters that can be compacted to fit within a tube can be positioned in the peritoneal by laproscopy placement, a minimally intrusive surgical procedure.

In view of the problems with the prior art outlined hereinabove, an object of the present invention is to provide a novel catheter device which has a large outer surface area to promote effective fluid exchange.

A further object of the invention is to provide a catheter with a generally flat design so that the catheter can be placed adjacent the peritoneal cavity wall, avoiding entanglement with the omentum, bowel, intestines, or other objects within the peritoneal cavity, yet still provide a large surface area for fluid exchange.

A further object of the invention is to provide a catheter device in which the design inhibits occlusion of the fluid passageways, such as by incorporating slit shaped holes.

A further object of the invention is to provide a flexible catheter which can be compacted such that it may be inserted into the peritoneal cavity by the method of laproscopy placement.

BRIEF DESCRIPTION OF THE DRAWINGS

The invention will be presently explained and illustrated by describing preferred, but not limitative embodiments thereof, with reference to the accompanying drawings, where.

DESCRIPTION OF THE PREFERRED EMBODIMENTS

Figure 1:
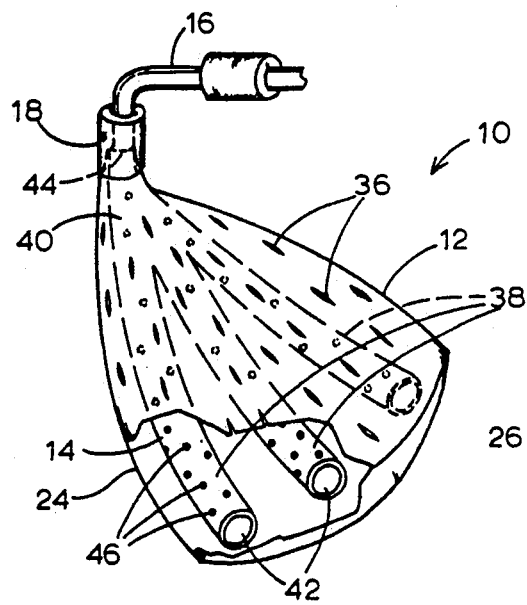
FIG. 1 illustrates a perspective, partial sectional view of the preferred embodiment of the catheter.
Figure 2:
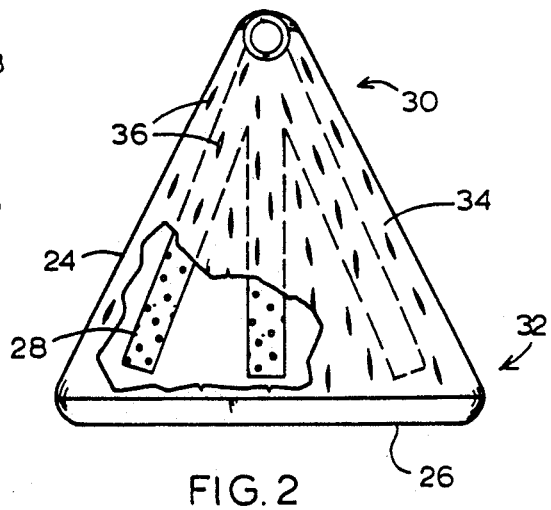
FIG. 2 illustrates a top view of the catheter of FIG. 1.
Figure 3:
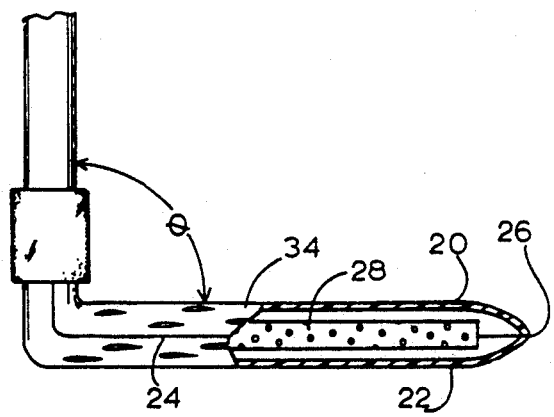
FIG. 3 illustrates a side view of the catheter of FIG. 1.

With reference in particular to FIGS. 1, 2 and 3, there is generally indicated at 10 the catheter of the invention. In the preferred embodiment, the catheter comprises a cover, or envelope structure, 12 and inner ductwork, or fluid distribution structure, 14. The cover and inner ductwork are connected by an appropriate method, such as by gluing. Ductwork 14 and connecting, or source, conduit 16 can be manufactured in one integral unit. In another embodiment, ductwork 14 and conduit 16 can be manufactured as two pieces. In such a case, ductwork 12, conduit 16 and envelope 12 may be connected at the same connecting point. In the preferred embodiment a dacron cuff 18 is secured over the connection point. However, dacron cuff 18 can be secured at any point along conduit 16. In addition, several dacron cuffs can be used to secure the catheter.

Referring more particularly to FIG. 3, in the preferred embodiment the cover comprises a first plate 20 connected to a second plate 22 about their perimeters along side edges 24, and end edges 26. Together, the plates form a chamber, or cavity, 28.

As shown in FIG. 2, the outer envelope structure creating the inner chamber is generally fan-shaped, having a narrow end 30 and a wide end 32. The two plates comprising the envelope structure are attached at their narrow end to the source tube mentioned earlier. In the preferred embodiment, as shown in FIG. 3, the source tube and dacron cuff are positioned at a 90 degree angle, $\theta$, from the generally flat expanse 34 of the first plate. However, other angles (not shown) can be used depending on where the catheter is placed within the peritoneal cavity.

In the preferred embodiment, the plates comprising the envelope structure are approximately 3" in length along their side edge, and approximately 2½" in width along their end edges. The plates are spaced generally ½" apart, to form an inner cavity generally 3" long, 2½" wide at its widest point, and ½" in depth. The plates are manufactured of a flexible, resilient biocompatible material with a non-adherent surface, such as polytetrafloroethylene or silicone.

As shown in FIGS. 1 and 2, the plates are fluid permeable. In the preferred embodiment, the fluid permeable or fluid communication structure comprises slits, or slit shaped holes 36. In the preferred embodiment the slits are approximately 1/16" to ½" in length and are approximately 1/32" in width. Such coaptable slits allow fluid to flow between the exterior of the envelope structure and the enclosed chamber. The slit shape of the holes discourages tissue or fibrin adherence to the holes, thereby preventing occlusion of the holes. The slit shaped holes discourage tissue adherence because the slit is generally long and narrow in shape thereby preventing folds of fat or fibrin, generally, round in shape, from wedging into the slit. In contrast, round holes of the prior art, having the same sized area for fluid flow, have a wider width, ideally shaped for folds of fat and rounded fibrin to wedge themselves in the round hole. Thus, the slit shape of the present invention allows the same fluid rate of the prior art while discouraging fluid passageway occlusion.

In addition, due to the slit shape of the holes, more holes can be cut in the outer surface of the catheter than round holes of the prior art. Thus, slit shaped holes can have a smaller opening surface area than round holes of the prior art, while the catheter of the invention achieves the same flow rate of prior art catheters. Use of these smaller slit shaped openings leads to less tissue adherence than the round holes of the prior art.

Further discouraging occlusion of the fluid passageways, the outer surface of the envelope structure is manufactured of a non-adherent material, such as polytetrafloroethylene. Thus, the combination of a non-adherent surface and slit shaped holes is an improvement over the prior art in that fluid passageway occlusion is decreased.

Positioned within the cavity formed by the plates is the fluid distribution structure, which comprises a system of tubes. In the preferred embodiment the fluid distribution structure 14 comprises three round tubes 38 which converge in a manifold region 40. In the preferred embodiment, the tubes and the connected manifold region are manufactured as one unit. However, in other embodiments (not shown) single tubes can be connected to a separately manufactured manifold section wherein the combination is then placed within the envelope structure chamber.

In the preferred embodiment, the ends 42 of the tubes are open. In other embodiments (not shown), the tubes can be manufactured with closed or sealed ends. Opposite the tube ends, the manifold region has one opening 44, which in the preferred embodiment is connected to the source conduit by gluing.

The tubes and manifold region can be manufactured of silicone or any flexible biocompatible material. In the preferred embodiment, the tubes are approximately 3" in length and have an inner diameter in the range of ⅛" to ¼". The outer diameter is in the range of ¼" to ½".

Positioned along the length of the tubes are holes 46. The holes allow fluid passing from the source conduit into the tubes, to flow out through the tube holes and into the enclosed chamber. Once in the chamber, the fluid flows out through the slit shaped holes in the envelope structure discussed above. Each tube positioned within the chamber has numerous holes so that if some holes are blocked by tissue adherence, other holes will still allow fluid flow from the tubes into the chamber. Further adding to the improved flow qualities of the disclosed catheter, use of numerous tubes within the envelope chamber increases the number of fluid passageway holes over single inner tube devices, as shown in Valli, thereby decreasing the effect of occlusion of some of the holes. In the preferred embodiment, the holes in the tubes are approximately 1/20" to 1/10" in diameter.

Figure 5:
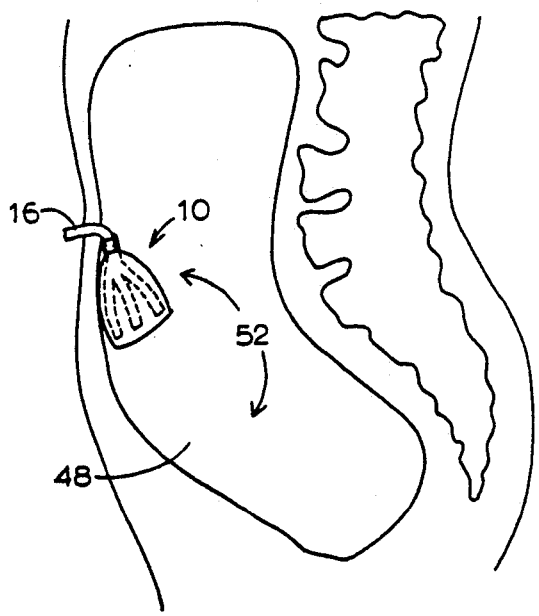
FIG. 5 illustrates the catheter of FIG. 1 positioned within the peritoneal cavity.

The preferred embodiment, utilizing three tubes, results in a large number of holes while maintaining a small bulk and generally flat shape of the catheter for placement against the wall of the peritoneal cavity, 48 (FIG. 5). Placement against the peritoneal wall avoids entanglement of the catheter with organs, as discussed above.

Figure 4:
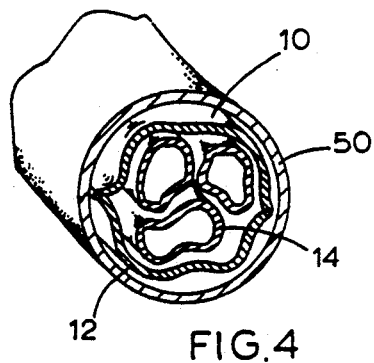
FIG. 4 discloses the catheter of the invention compacted within a surrounding tube for placement into, or withdrawal from, the peritoneal cavity.

Another improvement of the present invention over the prior art is that the invention comprising multiple flexible inner tubes and a flexible resilient outer cover can be compactly placed within a round tube for laproscopy placement into the peritoneal cavity as shown in FIG. 4. When compressed, the catheter 10, can be placed within a outer placement tube 50. During insertion of the catheter into the outer tube, the inner tubes 14 and the envelope structure 12 are pressed together into a generally round shape. Once in this generally round shape, the catheter is placed into the outer placement tube 50, whereby the catheter is then inserted through laproscopy placement into the peritoneal cavity. In the preferred embodiment, the placement tube is a 10 mm Trocar tube. Laproscopy placement is a minimally intrusive surgical procedure that does not require sutures after insertion of the catheter and from which the patient can quickly recover.

In the preferred embodiment, three inner tubes and a generally fan-shaped outer envelope structure are best suited for such laproscopy placement. However, different numbers or arrangements of inner tubes and different envelope structures, such as square or round designs, can be used.

Once the catheter is positioned inside the peritoneal cavity, the outer placement tube is removed, thereby allowing the flexible resilient inner tube and outer envelope structure to expand to its relaxed fan-shape, shown in FIG. 1. In the preferred placement position, the catheter is placed in the middle or lower portion, 52, of the peritoneal cavity, adjacent the peritoneal cavity wall. Such placement allows effective fluid exchange during the dialysis procedure, yet discourages the catheter device from becoming entangled with the omentum, bowel, intestines or other organs. To secure the catheter against the peritoneal cavity wall, dacron cuffs are used. The dacron cuffs promote tissue adherence thereby anchoring the catheter against the peritoneal cavity wall.

Due to the improved occlusion preventing design of the present invention as discussed hereinabove, the catheter of the present invention can be placed in the peritoneal cavity for longer periods of time than catheters of the prior art. Once removal of the catheter is desired, the outer placement tube is placed around the source conduit of the catheter and inserted into the peritoneal cavity, compressing the catheter into a generally round shape within the outer placement tube. Once compressed, as show in FIG. 4, the placement tube, containing the catheter, is removed from the patient's body.

While the invention has been described with respect to several preferred embodiments, it will be appreciated that many other variations, modifications and applications of the invention may be made.

I claim:

1. A catheter device for dialysis comprising:
   ductwork comprising multiple tubes and a source conduit connected with the tubes;
   envelope structure forming a chamber encompassing the tubes;
   the envelope having an interior and an exterior; and
   the envelope being fluid permeable to allow fluid flow between the interior and the exterior of the envelope.

2. The catheter of claim 1 wherein the envelope is generally fan-shaped.

3. The catheter of claim 1 wherein the envelope includes slit-shaped holes therein to allow fluid flow between the interior and the exterior of the envelope.

4. The catheter of claim 1 wherein the catheter is constructed for insertion into the peritoneal cavity by laparoscopy placement.

5. A dialysis catheter comprising:
   a generally flat, elongate cover forming a generally enclosed cavity;
   fluid distribution structure positioned within the cavity; and
   the cover including communication structure therein to allow fluid flow into and out of the cavity.

6. The catheter of claim 5 wherein the fluid distribution structure comprises tubes.

7. The catheter of claim 5 wherein the cover is fan-shaped.

8. The catheter of claim 5 wherein the communication structure comprises holes.

9. The catheter of claim 12 wherein the holes are slit shaped.

10. The catheter of claim 5 wherein the catheter is placed into the peritoneal cavity by laparoscopy placement.

11. A catheter device for dialysis comprising:
    an elongate, double-walled catheter assembly having fluid permeable walls wherein dialysis fluid flows through an inner wall and then through an outer wall when exiting the catheter, the outer wall having a generally flat shape when in an expanded form.

12. The catheter of claim 11 wherein the inner wall is tube shaped.

13. The catheter of claim 12 wherein the outer wall has a fan-shaped exterior surface such that the catheter includes a narrow end and a wide end.

14. The catheter of claim 13 wherein the outer wall has slit shaped holes therein for fluid flow.

15. The catheter of claim 11 wherein the catheter is constructed of flexible resilient material such that the catheter can be compressed for insertion into the peritoneal cavity by laparoscopy placement.

* * * * *